US006663777B2

United States Patent
Schimel (10) Patent No.: US 6,663,777 B2
(45) Date of Patent: Dec. 16, 2003

(54) APPARATUS, SYSTEM, AND PROCESS FOR ANAEROBIC CONVERSION OF BIOMASS SLURRY TO ENERGY

(75) Inventor: Keith A. Schimel, 330 Apple St., Syracuse, NY (US) 13204

(73) Assignee: Keith A. Schimel, Syracuse, NY (US)

(*) Notice: Subject to any disclaimer, the term of this patent is extended or adjusted under 35 U.S.C. 154(b) by 0 days.

(21) Appl. No.: 10/095,790

(22) Filed: Mar. 12, 2002

(65) Prior Publication Data

US 2003/0173291 A1 Sep. 18, 2003

(51) Int. Cl.[7] .................................................. C02F 3/28
(52) U.S. Cl. ....................... 210/603; 210/612; 210/614; 210/138; 210/143; 210/258
(58) Field of Search ............................... 210/603, 612, 210/614–617, 630, DIG. 9, 138, 143, 200–202, 252, 258, 259

(56) References Cited

U.S. PATENT DOCUMENTS

| 4,375,412 | A | | 3/1983 | Schimel |
| 4,401,565 | A | | 8/1983 | Schimel |
| 4,614,588 | A | * | 9/1986 | Li ................................ 210/603 |
| 4,642,187 | A | | 2/1987 | Schimel |
| 4,824,571 | A | * | 4/1989 | Ducellier et al. ............ 210/603 |
| 4,986,916 | A | * | 1/1991 | Hickey ........................ 210/603 |
| 5,180,494 | A | * | 1/1993 | Yamaguchi et al. ......... 210/603 |
| 6,296,766 | B1 | * | 10/2001 | Breckenridge ............... 210/613 |

FOREIGN PATENT DOCUMENTS

| DE | 19538387 | * | 4/1997 |
| EP | 1236688 | * | 9/2002 |
| JP | 7-171592 | * | 7/1995 |

* cited by examiner

Primary Examiner—Fred G. Prince
(74) Attorney, Agent, or Firm—Thomas R. FitzGerald, Esq.

(57) ABSTRACT

An improved digester apparatus converts wet carbonaceous biomass materials to biogas in a digestion unit operating at a controlled temperature and having a concentrator component and a pressure swing component each containing anaerobic bacteria. The apparatus conveys slurried aqueous biomass from a biomass source to the concentrator component and removes the biogas from the concentrator component and conveys concentrated aqueous biomass from the concentrator component to the pressure swing component and conveys digested aqueous biomass from the pressure swing component to the concentrator component. The apparatus removes waste solids from the pressure swing component and a pressure swing pump controls the pressure within the pressure swing component in a cycle comprising a sub-atmospheric first pressure phase and a second pressure phase at or above atmospheric pressure. Included in the apparatus is a programmable computer provided with a database relating previously measured biomass-biogas conversion data for biomass materials of varying compositions to values for the first and second pressure phases. The computer operates to continuously monitor the pressure of biogas in the pressure swing component and adjust the cycle of the pressure swing pump to optimize biogas conversion of biomass from the biomass source.

40 Claims, 7 Drawing Sheets

Gas Production Rate vs. Time at Line 70

Fig 3. TAP Stage II: Simple Pressure Swing Cycle

FIG. 5c Fixed Full Position

FIG. 5d Fixed lower Position

FIG. 5e Floating Full Position

FIG. 5f Floating Lower Position

APPARATUS, SYSTEM, AND PROCESS FOR ANAEROBIC CONVERSION OF BIOMASS SLURRY TO ENERGY

FIELD OF THE INVENTION

The present invention relates to the anaerobic biological conversion of biomass such as industrial sludges, slurried refuse and agricultural residues to combined heat and power (CHP). More particularly, this invention relates to a system, a digestion apparatus, and a process for effecting the rapid and complete anaerobic hydrolysis of biomass comprising wet organic matter, and the ultimate conversion of soluble and gaseous byproducts to methane and, ultimately, to useful thermal or electrical energy.

BACKGROUND OF THE INVENTION

Anaerobic digestion (AD) is a technology having three main disadvantages that result in its rarely being considered for energy production. The principal disadvantage stems from the fact that the reduction in volatile organic solid material is frequently far from complete. The results depend on the substrate, but incomplete conversion is typical of systems in which water is the sole plasticizing agent and hydrolytic pretreatment is not employed.

The second disadvantage is the long hydraulic residence time or the length of time the liquid must stay in the digestion system to complete the transformation of the slowest metabolizing materials. Unless the digester is heated, the residence time in the digester can be very long, as much as 40 to 60 days. The third disadvantage is that conventional digestion is prone to failure caused by three types of overloads—organic, hydraulic, and toxic—that can result in the disruption of gas production. In this case, the digestion system must be taken out of service, the digester tank(s) cleaned out, and the system restarted. The environmental effects of such failures can be serious, particularly when other facilities for treatment are unavailable and raw sewage or untreated sludge must be disposed directly to the environment.

Incomplete solids hydrolysis is caused by two problems. First, biomass is a mixture of colloidal and particulate constituents that have very different hydrolysis rates. Some organic constituents are metabolized and degrade more rapidly than others. For example, common soluble chemical intermediates such as acetic acid and glucose, as contained in sugar waste waters, are constituents that degrade rapidly. On the other hand, constituents that degrade slowly or not at all include particulate and colloidal materials, such as proteins, fats, vegetable oils, tallow, bacterial and yeast cell walls, lignin and cellulose. Accordingly, the hydrolysis of the most resistant organic fraction becomes the efficiency limiting step since complete degradation can take place only after hydrolysis of all the insoluble constituents' has occurred. In conventional AD, the accumulation of unwanted digestion products wastes reactor space. The economic use of reactor space dictates that the diverse symbiotic bacterial mass and undigested material be efficiently captured and the spent materials be efficiently removed to ensure the hydrolysis of the slowest metabolizing materials. Incomplete hydrolysis and solids accumulation in conventional AD systems is generally responsible for the poor performance for these systems.

Conventional AD systems are prone to failure, and operational control has been problematic. Different biomass substrates can have very different degradative characteristics, or different ratios of easily degradable material to refractory organic material. This limits AD systems to one particular substrate and to a small loading range to insure continuous uninterrupted operation. The loading limits are determined by trial and error experimentation. To insure that the operation stays within the limits of digestion, AD operators monitor total gas production supplemented with intermittent analysis of pH, alkalinity and volatile solids testing of the mixed liquor. Error correction is accomplished by manually adjusting the flow rate and solids loading. However, the warning signs of imminent failure usually come too late. This haphazard process control methodology is insufficient to guarantee uninterrupted operation needed for energy production purposes.

Various approaches have been proposed for overcoming the shortcomings of conventional AD systems. The disclosures of all of the patents discussed in the paragraphs that follow are incorporated herein by reference.

Many investigators have shown the value in recycling solids between two reactors to maintain high substrate and bacterial enzyme concentrations. For example, in U.S. Pat. No. 4,559,142 to Morper, it is recognized that it is economically advantageous to process the more slowly hydrolyzable material in a second reactor, separate from a reactor where the more rapidly hydrolyzed material is treated. Other investigators have recognized the benefit of maintaining the second reactor at a higher temperature to increase hydrolysis of slower hydrolyzing materials. However, these patents do not teach the control of temperature and pressure cycling on the second digester to improve both the rate and completeness of the digestion process.

In U.S. Pat. Nos. 5,015,384 and 5,670,047 to Burke, mechanical or chemical enhanced mechanical means are used to thicken and separate the partially digested particulate constituents from the effluent stream and recycle the particulates back to the digester, saving substrate and bacterial enzymes to further the hydrolysis. In subsequent U.S. Pat. No. 6,113,786, Burke recognized the advantage of mechanically removing inorganic solids from the reacting medium in order to preserve reactor space for the partially digested organic solids. The Burke patents, however, do not suggest a process design that promotes in-reactor thickening while digestion and advanced hydrolysis is ongoing, nor do they teach the intermittent separation and removal of inorganic solids via short term gas expulsion during reactor blow-down.

Investigators have described the need to improve the digestibility or hydrolysis of wet biomass. In U.S. Pat. No. 5,785,852 to Rivard et al. is proposed an elaborate pretreatment scheme using a pressurized thermochemical and mechanical processes to liquefy 44–66% of the sludge solid prior to digestion. The resulting soluble mixture is then amenable to conventional AD and the inorganic solids washout with the system effluent. The Rivard patent does not suggest the use of in-reactor pressure swing digestion technique to improve the digestibility and hydrolysis of biomass, nor does it teach the reaction of gas plasticization via pressure cycling to disrupt the sludge integrity and enable the advanced hydrolysis of refractory particles.

In U.S. Pat. No. 4,642,187 and related U.S. Pat. Nos. 4,401,565 and 4,375,412, the inventor of the present application described a system for separating and routing the slowly hydrolyzable material into a second reactor gas-solid suspension. Anaerobic bacteria are contacted with an influent slurry containing solid organic material, refractory organic material, and undissolved inorganic material, which are captured and recycled between the reactors in a closed loop to achieve a high conversion of the organic material to gaseous products, including methane. It was observed that pressure cycling in this second reactor facilitates the rapid anaerobic breakdown of refractory particulates, as measured by maximum volatile solids reduction and total gas production.

This basic approach has enabled rapid refractory solids hydrolysis with the continuous maintenance of a high bacterial concentration within the system reactors to attain nearly full solids conversion. These factors have allowed a significant reduction in digestion tankage and thus have improved the economic factors involved in energy production. U.S. Pat. No. 4,642,187 and its related patents do not teach the method of tuning the pressure swing program, the nature of the second stage reaction, or a variety of modifications needed to enable a wide array of bioenergy applications. Neither do they teach or suggest an apparatus or process of driving the hydrolysis of refractory solids substantially to completion via gas plasticization.

Furthermore, in U.S. Pat. No. 4,642,187, the inventor of the subject application described a method and baffle assembly in the first stage concentrator tank that diverts the flow to assist in stripping the gas, thereby facilitating solid-liquid separation and sedimentation. Solids undergoing active digestion often have gas bubbles adhered to them, which changes their specific gravity and settling characteristics. However, if a gasified particle contacts the gas phase during a free-fall cascade, the gases easily transfer from the solid to the gas phase, essentially degassing the solid and enabling the solid to concentrate by gravitational settling. Passing the gasified particles through a submerged gas volume is a minimum cost method of accomplishing effective solids-liquid separation and thickening in anaerobic environments. U.S. Pat. No. 4,642,187, however, does not teach or suggest the additional use of submerged gas volume to collect a gas volume needed to offset volume losses occurring in the second stage vacuum digester.

SUMMARY OF THE INVENTION

The present invention is directed to an improved digester apparatus for converting wet carbonaceous biomass materials to biogas comprising gaseous organic fuel. The apparatus comprises a digestion unit operating at a controlled temperature and having a concentrator component and a pressure swing component each containing anaerobic bacteria and means for conveying aqueous slurried biomass from a biomass source to the concentrator component, and for removing the biogas from the concentrator component. The apparatus also includes means for conveying concentrated aqueous biomass from the concentrator component to the pressure swing component and for conveying digested aqueous biomass from the pressure swing component to the concentrator component, thereby forming a closed loop between the concentrator and pressure swing components. The apparatus further includes means for removing waste solids from the pressure swing component and a pressure swing pump for controlling the pressure within the pressure swing component in a cycle comprising a first phase having a first time duration at a sub-atmospheric first pressure and a second phase having a second time duration and a second pressure at or above atmospheric pressure.

The improvement comprises: inclusion in the apparatus of a programmable computer provided with a database comprising data relating previously determined biomass-biogas conversion for biomass materials of varying compositions to values for the first and second, respectively, pressures and time durations of the first and second phases, wherein the computer operates to continuously monitor the pressure of biogas in the pressure swing component and adjust the cycle of the pressure swing pump to optimize biogas conversion of biomass from the biomass source.

This invention, which extends the capability the anaerobic digestion (AD) to substantially complete the transformation of wet biomass to methane gas and energy products, makes use of an ordinary mixed culture of anaerobes, or a pure culture or a genetically modified organism(s) (GMO) to extract the maximum amount of energy from biomass immersed in water. Fully recovering the mass energy content under water is dependent on completing microbial mass hydrolysis. A unique pressure swing method that cycles between pressurization-depressurization and is computer controlled to optimize system efficiency and reliability is capable of superior hydrolysis performance in anaerobic digestion, particularly of difficultly degradable materials such as cellulose.

Accordingly, it is an object of the present invention to provide an improved anaerobic cyclic digestion system for converting wet organic biomass materials such as sewage sludge to useful energy by optimizing the process through computer control.

It is a further object of the invention to utilize a programmable computer to control the cyclic digestion process, monitor the process for conditions leading to reduced performance, and take corrective action to maintain optimum operation.

It is a still further object of the invention to utilize gas plasticization to improve the second stage hydrolysis and digestion in the influent material fed to the system.

It is a further object of the invention to utilize a computer to monitor the anaerobic sludge digestion process for indication of insufficient plasticization and take corrective action to improve gas adsorption and penetration and optimize the second reactor hydrolysis rate.

It is a further object of the invention to provide an improved method for continuously and automatically correcting for loss or gain in system hydraulic volume to accommodate in-reactor biomass thickening during active continuous digestion by providing a submerged gas volume that is filled with gas production in the first reactor and subsequently used to offset the volume loss in the second reactor.

It is a further object of the invention to provide an improved method for continuous and automatic solids capture by providing a submerged gas volume at the top of the first reactor.

It is a further object of the present invention to provide an improved method for removing inorganic solids, thereby preventing the buildup of inorganic materials and maintaining system digestion capacity during active continuous digestion.

It is a further object of the present invention to provide means for routing the ammonia-containing gas stream to the pressure side of the digestion system and thereby scrub the ammonia gas from the gas phase.

It is a still further object of the present invention to provide a means for scrubbing hydrogen sulfide gas, an undesirable combustion fuel contaminant that corrodes metals and produces sulfur dioxide, whose combustion leads to photochemical smog, from the biogas stream.

BRIEF DESCRIPTION OF THE DRAWINGS

and 4,642,187. Like reference numbers in FIG. 1 and the other figures refer to like elements.

DETAILED DESCRIPTION OF THE INVENTION

The present invention is an efficient and reliable biological method of converting organic matter submerged in water to useful forms of energy and accomplishes the conversion much faster and more complete than any previous Anaerobic Digestion (AD) art. The first reactor in the loop is used to convert easily degradable organic solids, primarily to grow and maintain a viable mesophilic or thermophilic methanogenic culture. The second reactor of the process is capable of completing volatile solids destruction via a unique gas plasticization mechanism and is especially useful for converting primarily refractory organic solids such as cellulose.

The apparatus of the present invention includes one or two tanks, a combination of pipelines, valves, and pumps, including pump means for repetitively cycling pressure in the apparatus between sub-atmospheric pressure and pressure at or above atmospheric pressure, and a programmable controller that is interfaced to a local personal computer or remotely controlled by an accessible file server of a larger computer. The present invention enables the generation of distributive heat and power at industries, wastewater treatment plants, and farms.

The applicant has observed that, when properly seeded biomass is treated with pressurized biogas, the entire substance rapidly swells and becomes softened. For the purposes of this disclosure, this process of swelling and softening is known as "gas plasticization", which can be generally defined as the use of the anaerobic digestion byproducts, biogas and, to a lesser extent, volatile acids and alcohols, to naturally soften and chemically alter solid surfaces. This process produces a substrate that is more easily degradable by anaerobic bacteria. Gas plasticization can be accomplished while the solids are undergoing digestion. The action is similar to plasticization by water, but, unlike water, biogas can penetrate into the native cellulose areas (crystallites). The plasticizing gases form weak covalent bonds at cellulose hydroxyl groups, effectively modifying the original crystalline structure. By continuously repeating the process, both the rate and degree of hydrolysis increases dramatically at relatively low temperatures and pressures. The applicant has observed that both the rate and extent of hydrolysis is a complex function of the contact time, the innate substrate quality, the type and amount of bacterial population present, the amount of accumulated inhibitors present, and the degree of plasticization that the biomass substrate has sustained. The observed exceptional volatile solids reduction achievable by this method includes significant protein destruction, as evidenced by nitrogen and ammonia evolution from the second reactor.

The applicant has devised subsystem improvements and companion computer feedback control to provide the following structural and computer control corrections, thereby insuring optimum combined heat and power (CHP) reliability and efficiency:

(a) structural corrections
  (1) solids capture correction: capturing bacterial enzymes and organic solids and preventing them from leaving the system helps protect against deficient gas production
  (2) volume correction: the system must provide a correction for loss or gain in system reactor volume caused by thickening and plasticization processes, thereby protecting against deficient gas production
  (3) ammonia gas correction: ammonia and hydrogen sulfide gas removal improves the biogas quality for combustion. Also, removal of ammonia in the gas phase can help protect against deficient gas production caused by microbial culture inhibition. For bioenergy applications, the presence of ammonia and nitrogen in the gas phase is undesirable because they dilute the BTU content of the fuel stream and form nitrous oxide, an air pollutant that causes photochemical smog on combustion. For waste treatment applications, ammonia nitrogen can be removed in the gas phase.
  (4) inhibition correction: allowing dissolved inhibitory substances to continuously leave the system in the process effluent to help protect against process inhibition that causes deficient gas production
  (5) inorganic accumulation correction: as solids conversion progresses over time, the byproducts of refractory degradation inevitably accumulate and occupy an ever increasing proportion of the reactor volume. The continuous or intermittent separation and removal of inorganic materials to prevent buildup helps protect against reducing the conversion efficiency, as observed by the slowing of gas production.

(b) computer control corrections
  (1) toxicity correction: the computer control system provides a correction for toxic overload events and thereby helps protect against deficient gas production
  (2) plasticization and thickening optimization: the computer control system optimizes the in-reactor thickening-plasticization process to protect against deficient gas production
  (3) hydraulic correction: the computer control system protects against deficient gas production by correcting flow fluctuations that diminish effective residence time
  (4) load correction: the computer control system helps protect against deficient gas production by providing a correction for organic overload
  (5) capacity correction. The computer control system provides a correction for diminishing volumetric capacity, timing the removal of grit and inorganic materials to maintain active digester space and optimum gas production.

Continuously reliable fuel delivery is of key importance to practical biomass-to-energy conversion systems. Computers can be used to control process variables and thereby optimize energy conversion. Real time sampling of sensor data (feedback) coupled to computerized corrective action in a closed loop enables a "smart digestion" system. Continuous monitoring of the dynamic biogas stream produced from the slowest metabolizing particulates in the second reactor provides data that define the rate limiting conversion reaction for the digestion system. An applied low pressure period effectively resets the over concentration of all volatile materials derived from the slowest metabolizing materials contained in the second reactor. Each pressure cycle is reset, starting the process from the same equilibrium point. Any change in gas production observed (derivative) early on in the pressure phase of the cycle is directly related to a change in the volatile solids destruction rate. Because a shift can be recognized almost immediately, immediate remedial action can be implemented through a feedback control loop. Optimally, four elements are desirable in an effective and scalable cyclic digestion control system:

(1) recognition: the controller must be capable of monitoring feedback signals from gas flow measuring, pressure transducer, and thermal sensing devices (2) understanding: the controller must reliably decipher the change in the rate of the feedback signal with respect to other information that is available or recognized (3) analysis: the controller must be able to deduce a diagnosis from the acquired information and be further be able to distinguish between the type of corrective action needed and a process or device error (4) response: the controller must be able take corrective action by changing pump flow rates and applied pressure duration times while the process is ongoing. To maintain optimum operating conditions, the response signal(s) must adjust the process pump appropriately, thereby varying feed and recycle flow rates, pressure amplitudes, and cycle frequencies and periods.

Figure 1:
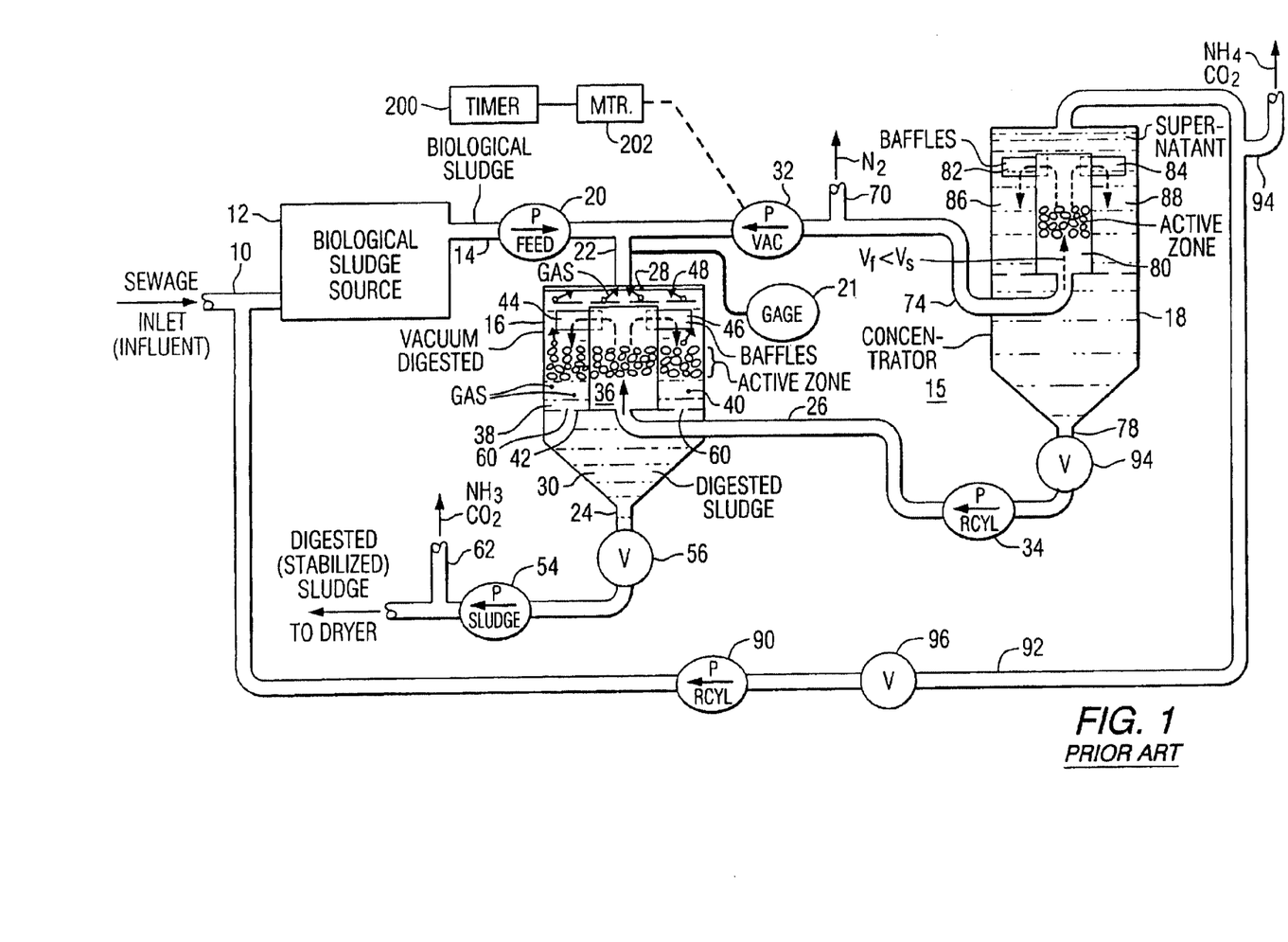
FIG. 1 illustrates a prior art anaerobic biomass digestion system described in U.S. Pat. Nos. 4,375,412; 4,401,565.

The present invention provides a substantial improvement to the anaerobic treatment process described in U.S. Pat. Nos. 4,375,412; 4,401,565; and 4,642,187, which disclose an anaerobic process wherein an influent stream containing organic particulate and soluble material is converted to gaseous products and soluble products. Referring to FIG. 1 of U.S. Pat. No. 4,375,412 (which is also FIG. 1 in each of U.S. Pat. Nos. 4,401,565 and 4,642,187), a schematic illustration is provided of an anaerobic pump (TAP) apparatus for carrying out an anaerobic treatment process that includes a biomass source, a first anaerobic reactor 18 and a second anaerobic reactor 16. The output from the biological sludge source is fed continuously into a closed loop system 15 containing two tanks 16 and 18, in which volatile solids conversion takes place. The influent is delivered to the first anaerobic reactor 18 along line 74 and contacted with anaerobic bacteria contained in the upflow partially fluidized bed 80.

The dual purpose of the centrally located partially fluidized bed is to foster rapid bacterial growth at the expense of partial digestion, followed by rapid liquid-solid separation. The upflow velocity ($v_f$) in the partially fluidized bed 80 is suitably less than the settling rate ($v_s$) for solid particles through water. For typical sewage sludge, this settling rate is approximately 2.7 centimeters per second. The rising particles exit the partially fluidized bed through baffles 82 and 84 and settle and concentrate in the outer peripheral settling chambers 86 and 88. Effluent from the first reactor 18 is delivered via recycle line 92 to biological sludge source 12 (or disposed to a sewer), forming a second closed loop. The gravity separated solids exit the first reactor at port 78 and are transmitted to the second reactor 16 through conduit 26 via recycle pump 34. The concentrated sludge enters the inlet of the second reactor, through the bottom plate 42 into the central passageway 36. The purpose of the second reactor is to foster a gas-solid suspension in outer passageways 38 and 40 that undergoes pressure cycling. A submerged suspension of solid particles supported by gases generated by anaerobiosis is retained in the passageway 36, 38, 40 during the pressure phase. During the low-pressure phase of the pressure cycle, the solid flow is downward against the vacuum via gravity, and the gas flow is upward via buoyancy toward the applied vacuum from pump 32. Pump 54 withdraws mineralized solids from the lower region 30 of the tank 16; these solids can be either recycled via line 62 or discharged to a drying bed or sewer. Ammonia and hydrogen sulfide gases can be removed in the biogas outlet stream 62. Capturing the biogas at the outlet stream 62 is preferred if process inhibition by these two dissolved gases is a likelihood or if removal from the process effluent 92 is needed.

The first reactor 18 preferably is sized to allow inlet feed 74 composed of influent feed 14 and recycle products 22 to contact anaerobic bacteria in the partially fluidized upflow reactor 80 for a specified period of time. After degrading a portion of the organic fraction to foster bacterial growth in the internal partially fluidized bed 80 of the first anaerobic reactor 18, the process concentrates the remaining organic particulate matter by stripping gases through a submerged gas volume formed by baffles 82 and 84. Solids settle and concentrate via gravity into the bottom zone 78. The Stage I effluent from the solid-liquid separation, composed principally of a small amount of unmetabolized colloidal and soluble fatty acid products of digestion, is recycled via line 92 to the biomass or sludge source 12, which can also serve as an aerobic polishing unit.

The first reactor 18 has inlet 10 that receives sewage or other biomass. A feed pump 20 feeds sludge from a sludge source 12 via outlet 14 to the reactor 18. The reactor 18 has outlets 22 and 24 at opposite ends thereof. The tank 18 is preferably maintained with its longitudinal axis vertical. The lower end of the tank may be conical in shape. The tank 18 has another inlet 26 for the concentrated and partially digested sludge from the concentrator tank 18. Inlet 26 enters the tank 18 between the region 28 at the top of the tank and a region 30 at the bottom of the tank. The pressure in the top region 28 is below atmospheric pressure and is a vacuum. The gauge 21 measures the vacuum in the region 28. A suitable vacuum pressure depends upon the scale of the system. In a small scale system a vacuum pressure of about −50 centimeters of mercury (gage pressure) has been found suitable. The optimum vacuum range is between −30 to −50 cm Hg gage vacuum. The amount of vacuum needed to maintain the solids in suspension is dependent on the character of the solid (i.e., the solid biodegradability). A plate 42 with holes 60, is disposed at the bottom of the passageways and baffles 44 and 46 attached to an upper plate 48 are disposed at the top of the passageways 36, 38 and 40. Gas is drawn by the vacuum in the upper region 28 through openings which form the passageways 36, 38 and 40. The gas has been found to consist essentially of nitrogen ($N_2$) with some methane ($CH_4$) released from time to time in small amounts. This gas may be withdrawn through a gas outlet 70 on the pressure side of the vacuum pump 32. Supernatant may be recycled back into the activated sludge unit by means of a recycling pump 90 through the feed lines 92. A gas outlet 94 for the methane and carbon dioxide resulting from the partial digestion of the sludge in the tank 18 is also provided. In the event that the recycling of the supernatant from the top of the concentrator tank 18 is used (such recycling is optional and is desirable when additional dissolved organic contaminant removal is needed), its flow is adjusted by the valve 98.

Figure 2A:
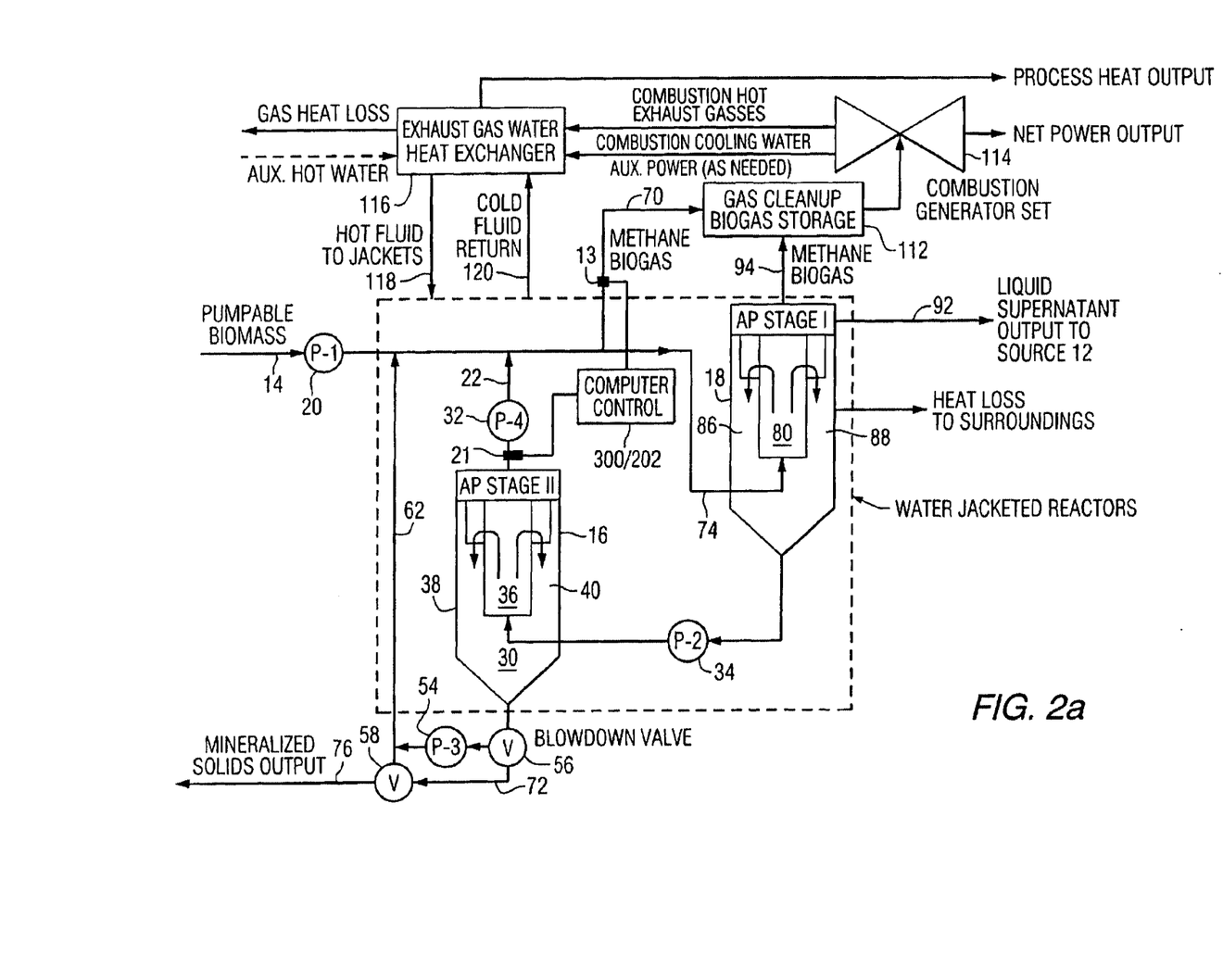
FIG. 2a is a schematic illustration of a two stage preferred embodiment of an apparatus for carrying out the process of the present invention.
Figure 2B:
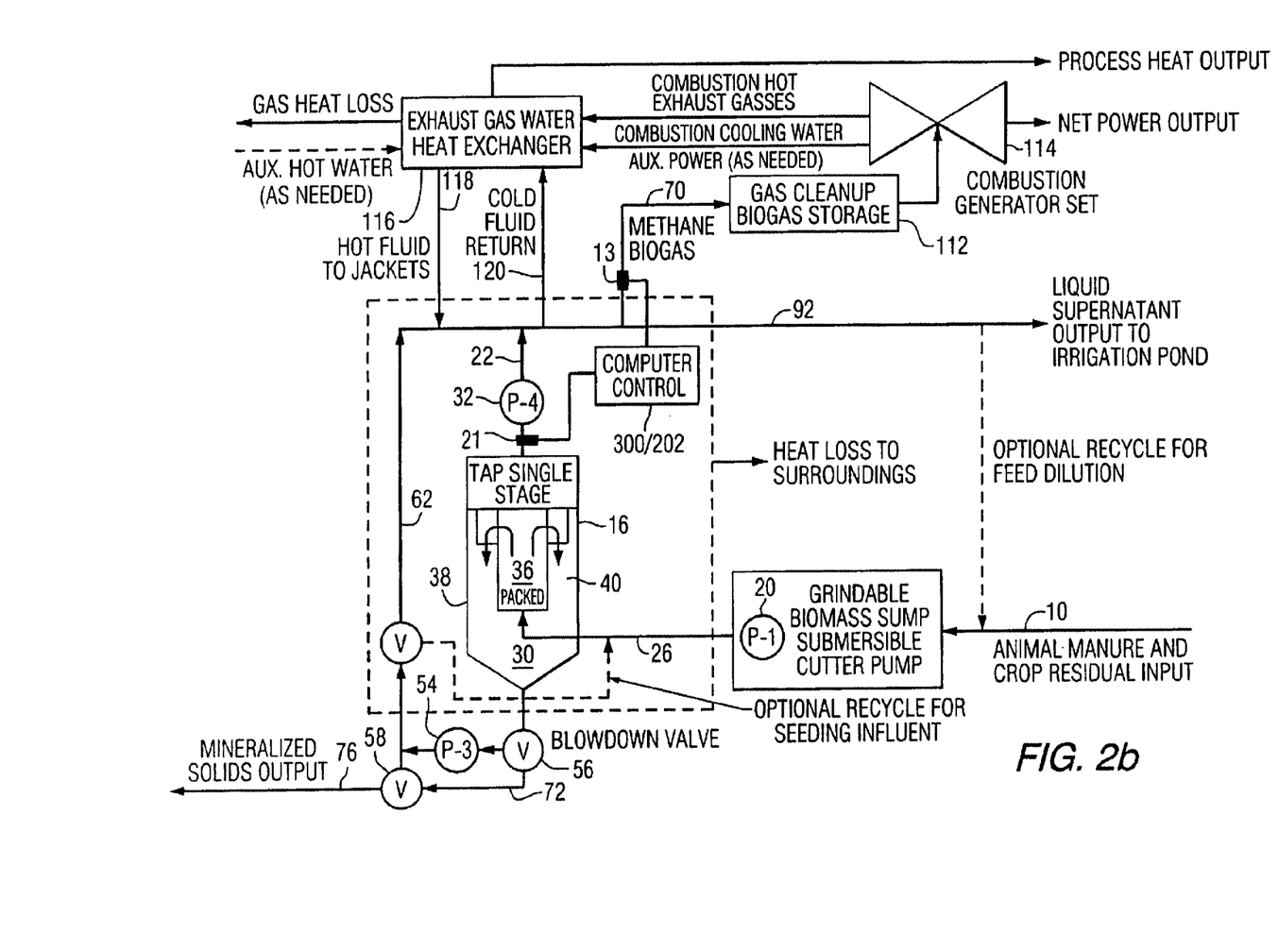
FIG. 2b is a schematic illustration of a one stage preferred embodiment of an apparatus for carrying out the process of the present invention.

FIGS. 2*a* and 2*b* are schematic illustrations of systems for carrying out the biomass-to-energy-process in accordance with the process of the present invention. The embodiment depicted in FIG. 2*a* comprises a two-stage digestion unit comprising first reactor 16 and second reactor 18, a gas storage and cleanup unit 112, a combustion engine-generator set 114, and an exhaust gas heat exchanger 116. The methane-biogas streams 70 and 94 convey biogas produced to a storage unit, for example, a conventional gasbag or water sealed inverted bell gas holder. Gas storage unit 112 may be affixed atop the first reactor 18 or located at the confluence of conveyance lines 70 and 94. Sulfur gas cleanup can be accomplished by, for example, a solid phase method using Iron Sponge, available from Connelly-GPM Inc., or a liquid phase method using SULFA-CHECK™, as described by Nalco/Exxon Energy Chemicals. Gas sweetening is optional and depends on the requirements of air pollution laws and the need to protect the generator set from corrosive gases.

The produced biogas may require pressurization prior to transfer to the engine generator set 114. Conventional combustion engine generator set 114 may be, for example, part of a complete combined heat and power apparatus 114 and 116 such as the Perkins 2000 Series (UK) or Perennial Energy Inc (MO, USA) apparatus. Gas flow measurement 13 can be accomplished by either dry, liquid ultrasonic (Doppler and transit time) or electromagnetic type apparatus, the choice depending on required measurement accuracy over a fluctuating flow rate range. The digestion portion of the system comprises a digestion apparatus similar to that employed in the prior art apparatus depicted in FIG. 1. A prior art digestion apparatus shown in FIG. 6 in each of U.S. Pat. Nos. 4,375,412 and 4,642,187 is identical to that depicted in FIG. 1, except for the inclusion of a timer 200 and a pump drive motor 202. Timer 200 is used to change the speed of pump 32 after specified discrete time intervals, e.g., one hour and seven hours.

The system of unit processes shown in FIG. 2*a*, which forms a very efficient combined heat and power (CHP) process, is the preferred embodiment for weakly concentrated organic solid slurries of 5% w/w solid or less. The continuous flow two-stage process is applicable to large scale wastewater treatment for agricultural and industrial applications. The concentrate from the first reactor 18, which is composed mostly of undigested colloidal and particulate matter, is pumped to the second reactor 16 via a pump 34. The mass transformation to gas is completed in the second reactor 16, which is operated in a pressure swing mode. In accordance with the present invention, the pressure swing operation in the second reactor 16 is controlled by a programmable computer 300 that detects changes in gas production using a measuring device such as a linear pressure transducer 21, together with pump-controlling means 202, for example, a variable-speed motor, which adjusts the pump head speed of pump 32 in accordance with the present invention. Computer 300 is further optionally provided with a device 13 for measuring biogas flow in line 70.

The system shown in FIG. 2*b*, which comprises a single-stage cyclic pressure digestion unit 16, a gas storage and cleanup unit 112, a combustion engine-generator set 114, and an exhaust gas heat exchanger 116, represents a very efficient combined heat and power (CHP) process that can be advantageously employed for small scale, high solids (5–10% solid) situations such as farm and MSW applications. Both FIGS. 2*a* and 2*b* illustrate the preferred positioning of energy conversion device 114 and heat recovery apparatus 116 following the reactor(s) 16 (and 18) and the connection of the biogas discharge lines 70 and 94. The waste heat recovered by apparatus 116 can be used to produce steam for industrial applications, or the steam can be directed into a steam turbine to produce additional electricity. Combined cycle plants of this type can increase their efficiencies up to 50–60%.

Gas plasticization and thickening represents a method of pressure manipulation that enables the recovery of the maximum amount of energy from an organic solid fraction. Full solids plasticization is necessary to achieve substantially complete conversion of refractory organic materials because otherwise these substances remain too brittle and resistant for anaerobic hydrolysis to occur. Without effective hydrolysis, these substances accumulate, wasting reactor space, require separation from the system and eventually ultimate disposal.

The present invention exploits a unique successive gas plasticization and thickening process to enhance anaerobic digestive mechanisms, in particular, the hydrolysis of refractory organic materials. Although gas plasticization has some similarity to plasticization by water, it is well known that water cannot enter the native crystalline structures. Gases, on the other hand, can enter crystalline structures and thereby permanently change the physical properties of biomass. The physical adsorption of biogas on solid surfaces that occurs during the applied pressure phase of the pressure program applied to the second reactor 16 causes surface deformations that are measurable by observing the viscosity hysteresis and are indicative of slurry thixotropic rheology. By repeating the compression-decompression cycle and thereby repeatedly deforming the solid structure, a suspension of semi-elastic or partially gelatinized solids is formed. On decompression, the gas accumulation is rapidly released (blowdown), and the applied low pressure is sufficient to overcome the forces responsible for the poor gas-liquid or mass transfer rates typical of thick digestion environments. The cyclic compression-decompression prepares the solid surface for increased microbial enzyme action and produces a facultative-methanogenic culture in which the anaerobic activity is far superior to that found under normal equilibrium digestion conditions.

The conversion efficiency is maximized by sequentially and repetitively executing the steps of the pressure swing adsorption (PSA) cycle depicted in FIG. 3, as follows: rapid pressurization of a low pressure suspension, gas plasticization and thickening of the pressurized suspension, rapid decompression of the suspension, and low pressure stripping of gas. Upon termination of the decompression phase, the slurry is fully degassed. Degasification and thickening are simultaneous processes occurring at low pressure, resulting in settling of the solids to occupy the degassed volume. There is then a transition to high pressure, where the gas plasticization process occurs. During this period of relatively high pressure, the nascent gas bubbles produced by the anaerobic action accumulate in the solid particle voids, creating a suspension held in passageways 38 and 40. The growing gas volume produced by digestion of the solids displaces the interstitial fluid upward out of the reactor as recycle effluent at 22. Next, during the applied decompression phase of the pressure program, the gas bubbles rise through the suspension, effectively weight classifying the suspension by gas density differential classification, allowing the lighter volatile organic solids to rise in the column and the heavier mineralized solids to fall downward. The continuous displacement of liquid upward and digesting solids downward effectively accomplishes automatic thickening in the second reactor 16. In-reactor thickening results in improved process stability with respect to organic overloading by effectively increasing the solid residence time, increasing the solution pH, and increasing the substrate concentration. It is the mechanism of sequential plasticization and thickening that enables the substantially complete solids conversion at room temperature of organic particles having very different hydrolysis rates.

Cellulose is an example of a major component of most biomass feedstocks that, because of its crystalline structure, is resistant to degradation by anaerobes. However, digestive byproducts can be used as gas plasticizing agents to initiate the dehydration of cellulose and other complex polysaccharides. Anaerobic plasticizing agents include polyhydric "sugar" alcohols, volatile fatty acids, and the gases of anaerobiosis: ammonia, hydrogen, carbon dioxide, methane, and hydrogen sulfide. Regardless of the chemical differences among the various agents, the overall conversion efficiency is dependent on whether the treatment is sufficient to derivitize native cellulose, presumably by forcing it to form a covalent bond with the plasticizing agent. When cellulose is derivatized, the fibers are chemically modified, and the plasticized material is said to be "partially gelatinized". The cellulosic solid thus becomes compressible whereas the surrounding liquid is incompressible. While the cellulose derivative is in a "plastic" state, the cellulose is well oriented for bacterial attack from a high density anaerobic population grown on the organic mass surfaces in the first reactor 18. In the second reactor 16, these high density fermentation enzymes hydrolyze the plasticized long chain molecules. The moisture level within the reactor needs to be controlled to be at least 50% or more to assure proper expansion for the desired degree of plasticization. A solids residence time of about 2 to 5 hours is sufficient to plasticize the admixture at room temperature and 1.5 atmospheres. The fermentation mixture containing a high concentration of facultative anaerobic bacterial cells is held for the appropriate plasticization time in the second reactor 16. As the cellulose decomposing enzymes secreted by the facultative anaerobic bacteria convert the fibers into much shorter ones, the particles become much smaller, and the plasticizing operation in the second reactor is greatly facilitated because the increasing surface area can support an ever increasing bacterial population. Fermentation mixtures having lower moisture content require higher pressures, and higher moisture formulations require lower pressures, to achieve the same results. It is beneficial to pre-soak with water or preheat the feed mixture to initiate plasticization under suitable plasticizing conditions. The digestion of refractory solids in cellulosic herbaceous biomass materials is thereby greatly accelerated.

Biomass materials frequently contain substantial levels of bacterial pathogens such as, for example, fecal streptococci. The waste solids produced by the process of the present invention are substantially free of bacterial pathogens.

The preferred embodiment of the present invention uses programmable computer means 300 with proportional, integral, and differential (PID) capability to control the rate and extent of solid gasification in the second reactor 16. There are many modified pressure swing adsorption (PSA) cycles, as known in the separation industry and as schematically depicted in FIG. 3, that can be applied to a variety of designs with multiple adsorption beds in parallel or series configurations. PSA configurations, i.e., purge and backfill steps, can be designed to optimize the kinetics of gas transfer for various mixtures and enzyme-catalyzed adsorbent mediums. Thus, for anaerobic systems, various PSA configurations can be applied to mixed culture anaerobic systems as well as to fermentation systems that involve pure or genetically altered organisms (GAO) cultures.

In anaerobic pressure swing, however, the overall kinetics of enzyme catalyzed gas-solid reactions is more complex than simple gas separation via adsorption. There are multiple biochemical pathways complexed with competing mechanisms. The pressure swing amplitudes and phase durations required to drive transformations are nonlinear functions of a combination of matrix characteristics and process physical variables. At a minimum, the kinetic performance is dependent on the mass biodegradability (including percentage cellulose), mass transfer characteristics, solid permeability and adsorptive capacity, gas concentration, substrate (solid) concentration, temperature, and pressure. Assuming reliable isothermal conditions, however, it is only necessary to capture the gases produced and control the critical variable, applied pressure. The multivariate complex problem is thereby reduced to just one process control variable. A record of each applied pressure cycle is measured by monitoring the gas production 13 on line 70 throughout the cycle shown in FIG. 3. The gas production pattern is digitally logged for each cycle, forming a historical database. The current gas production pattern is compared to the recent pattern records to detect and flag any errors or deficiencies that are recognized. The points of differential change between current and recent historical gas production patterns are calculated in near real time. Significant pattern and differential changes trigger a real-time corrective feedback to improve production, the appropriate response being selected from a subset of allowable responses. The magnitude of the response can be based on some probabilistic rule or be simply proportional to the magnitude of the change. The default response is the "do nothing" response.

The preferred embodiment of the present invention uses a programmable computer 300 to monitor biogas production at line 70, pressure at 21, process temperature in the water jacket return 120, pump flow rates 34, 54, and 32, and valves 56 and 58. Computer 300 and pump drive motor 202 control vacuum pump 32, which operates cyclically to produce faster flow for a period of time, then slower flow for a period of time. As the solid volume is reduced due to advanced hydrolysis, the incoming solids from passageway 36 enter the passageways 38 and 40, displacing liquid upward, continuously replenishing and concentrating the solids in reactor 16. The rapid decompression step shown in FIG. 3 releases the gases accumulated during the previous plasticization phase. Computer 300 causes valves 56 and 58 to open, exposing the reactor 16 contents to near atmospheric pressure. The compressed gases that have accumulated expand toward the low pressure outlet at valve 56 and 58. Recycle pump 34, controlled by computer 300, runs at a constant rate that corresponds to the rate of volume turnover in the digestion system. The pressure regulating program of the present invention uses computer 300, shown in FIGS. 2a and 2b to adjust pump speeds after comparing the time derivative of the feedback variable to the stored historic value. (This function could not be performed by the timer 200 shown in prior art FIG. 6 of U.S. Pat. Nos. 4,375,412 and 4,642,187.) New set-points are calculated for the next cycle; when the elapsed time set-point is reached, the pressure program triggers a change of the pump drive motor 202 voltage to reach the new time or pressure setpoint. A change in pump 32 flow rate causes more or less flow to exit the second reactor 16 at 22 and varies the pressure therein between a pressure below atmospheric and above atmospheric pressure. For room temperature (20° C.) operation, a low cellulose substrate (relatively high biodegradability) program would have, for example, an amplitude and phase of about 0.5 atmosphere of low pressure for one hour and about 1.5 atmospheres of high pressure for one hour. By contrast, a relatively high-cellulose substrate (low biodegradability) program would have, for example, an amplitude and phase of about 0.5 atmosphere of low pressure for 1 hour and about 1.5 atmospheres of high pressure for 3–4 hours. Increasing the digestion temperature will increase the biochemical reaction rate proportionately. A unit increase in reactor temperature enables the pressure amplitude and phase duration to be decreased proportionately to achieve the same results.

Figure 4A:
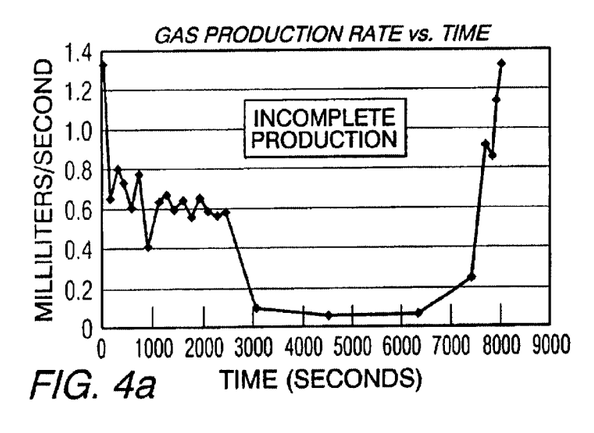
FIGS. 4a–4d are graphs illustrating the real time correction of the biogas output of the pressure swing program for the second reactor.
Figure 4B:
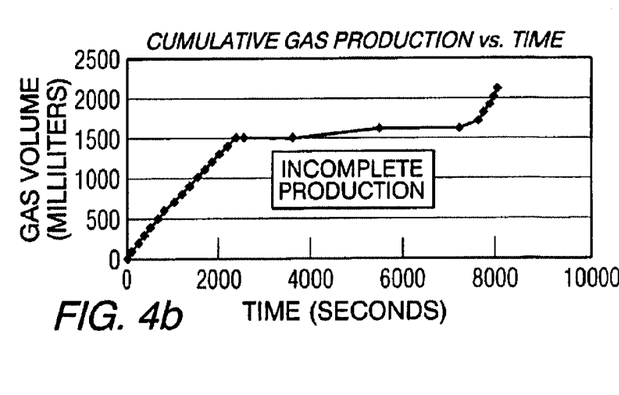
Figure 4C:
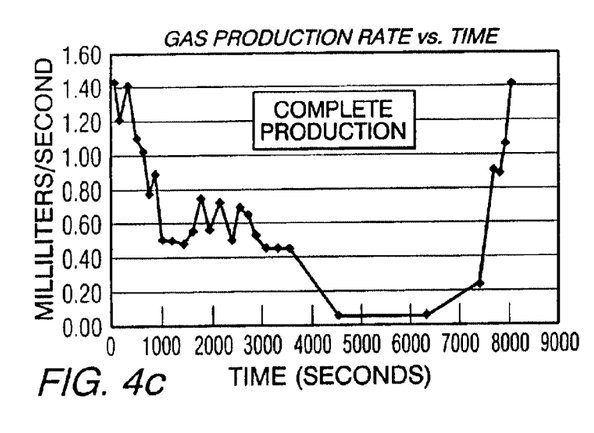
Figure 4D:
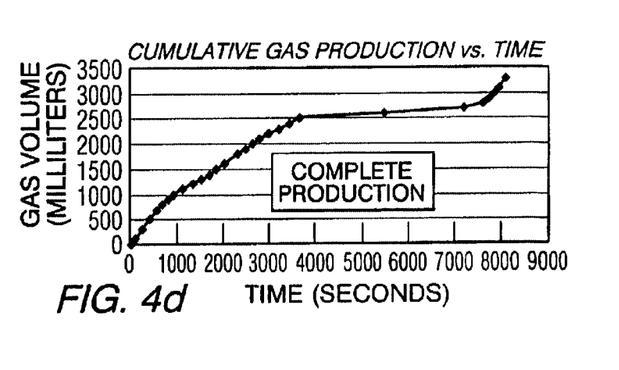

The process control computer 300 employs pattern recognition capability to continuously track and optimize the gas production and solids conversion in the second reactor 16. The most important portion of the gas production pattern is acquired during the low pressure decompression phase, which is compared to logged patterns produced at the outlet 70. As shown in FIGS. 4a and 4c, the discharge of the gas accumulated during the compression phase causes the derivative to oscillate and requires a considerable settling time of approximately ½ hour to reach a consistent production level. The applied low pressure effectively zeros out the gas accumulation in the second reactor 16. The gas production at line 70 provides a characteristic reproducible gas production pattern. Each pattern is digitally logged, the discrete point measurements being preserved for derivative analysis and for providing a historical record for future comparisons. As a new production segment is being acquired, the previous segment is being scanned for deficiencies. During each scan in background, the process control computer discriminates between properly formed and deficient gas production patterns that are the object derivative analysis. For example, FIG. 4a and its integral FIG. 4b show a deficient gas production pattern, where production falls off prematurely to almost zero at the 2500 second mark of a one hour low pressure decompression period. In this example, approximately 110 seconds of gas production time is wasted. The accumulative loss over time causes deficient gas production that has a considerable negative effect on performance. In this case, it is unlikely that the premature falloff is due to inadequate bacterial density, since loading to and gas production from the first reactor 16 has remained constant, an indication of good culture activity. Instead, the abrupt falloff is most likely due to insufficient plasticization time during the compression phase of the cycle. Depending on whether the gas production is increasing or decreasing from previous measurements determines whether the time derivatives are positive or negative. For the positive derivative, proportionately increasing the plasticization time will correct the error and yield the improved gas production pattern shown in FIGS. 4c and 4d. The process response specification requires PID computer 300 to correct for the production deficiency over several cycle periods or a few hours. The most recent output pattern at 70 is compared to the historical pattern record to diagnose deficiencies and formulate and execute a corrective action in that time frame. Since the wide range of biomass materials is characterized by greatly differing hydrolysis rates, a relatively short response time is crucial. Continuous process tuning is required to correct for changes in hydrolysis time and enable the conversion of a variety of materials without process slowing and shutdown. This method of continuously adjusting control parameters allows the process to accommodate large changes in feed material characteristics or loading without experiencing weak performance. Switching from one slurried fuel to another becomes seamless. Typical process ailments such as incomplete plasticization, hydraulic overload, organic overload, toxicity and insufficient acclimation time will take only a few cycles, measured in hours, to detect, diagnose, and correct. Unmanned process monitoring and adjustment can routinely prevent anaerobic fermentation failure that generally occurs over a much longer time frame.

Figure 3:
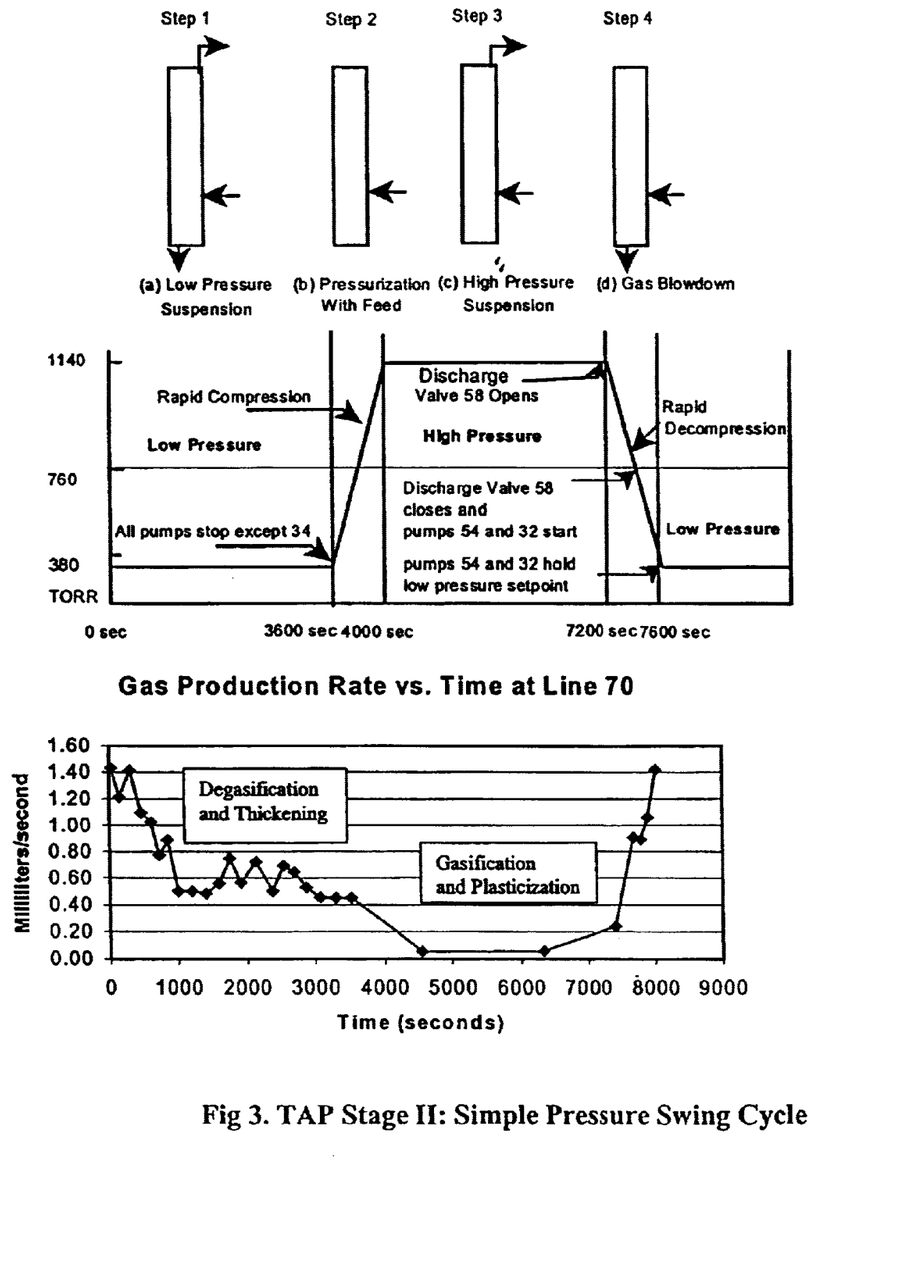
FIG. 3 is a schematic diagram of the timing sequence of a simple pressure swing control program applied to the second reactor of the apparatus of the present invention.

A well tuned PID-controlled process can ramp up or down to reach pressure set-points within minutes, as shown in FIG. 3. The response specification is based on overshoot, rise time, decay ratio, and settling time that is initialized during process startup. These initial specifications are established during clean reactor pressure tests. Default PID parameters for process gain, time constant, and time delay are estimated based on the analysis of the transient response of the closed loop system to setpoint changes or load disturbances. These parameters can be calculated using "modified" Ziegler Nichols tuning. During operation, the discrete data are analyzed for error derivatives in background to pinpoint performance changes. The working specification based response adjustment is a continuous process. Because of the superior response of PID control to pressure or time setpoint changes, response adjustments are generally much faster than slow developing process perturbations that affect the gas production patterns illustrated in FIGS. 4a–d.

Figure 5A:
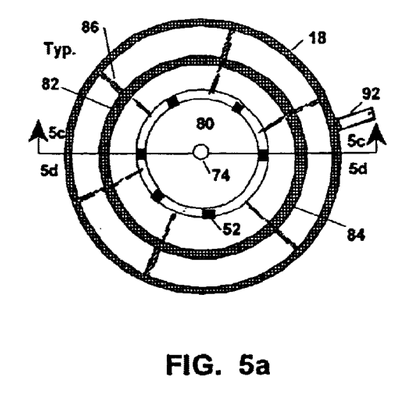
FIGS. 5a and 5b are sectional plan views of a first reactor 18 in the system view taken along the lines 5a—5a and 5b—5b in FIGS. 5c and 5e.
Figure 5B:
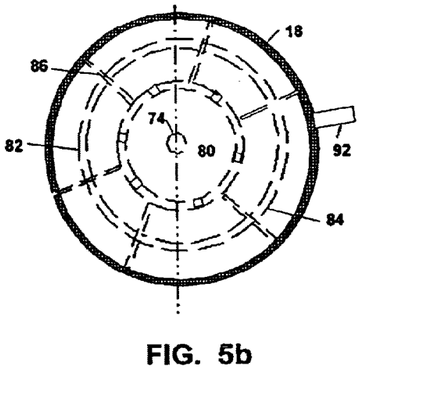
Figure 5C:
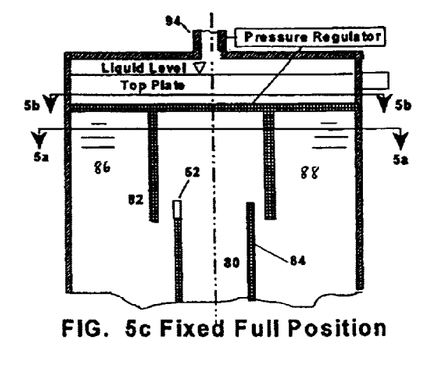
FIGS. 5c–5f are fragmentary views in elevation of the upper portion of the first reactor 18 in the system of FIGS. 2a–2b, illustrating either a fixed or floating submerged gas volume in a raised or a lowered position.
Figure 5D:
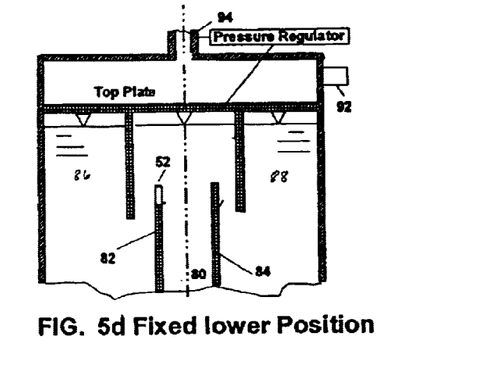
Figure 5E:
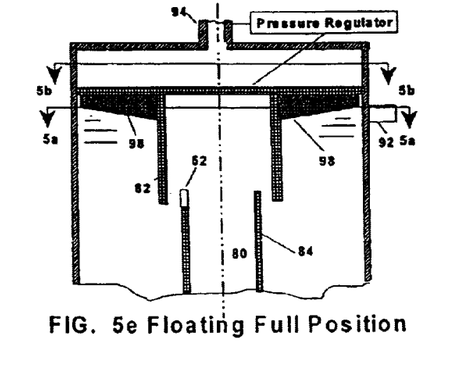
Figure 5F:
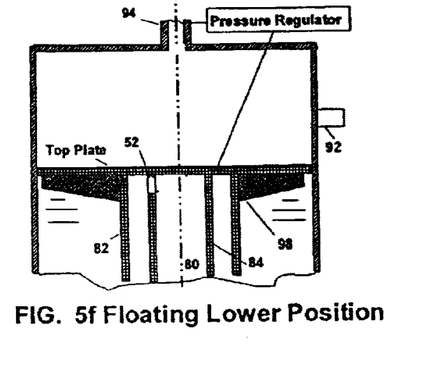

Any loss of digestible organic solids in the process effluent 92 from the first reactor 18 reduces process performance. To prevent this, reactor 18 is provided with either a fixed baffle assembly, as shown in FIGS. 5c–d, or an internal floating roof assembly, as shown in FIGS. 5e–f, is used to capture enough gas volume to make up the volume lost in the second reactor 16. In a preferred embodiment for small volume makeup, the first reactor 18 contains an internal fixed baffle assembly, shown in FIGS. 5c–d, that consists of cylindrical volume forming fixed inverted baffles 82 and 84 attached to a top plate, thereby creating an underwater baffle assembly above and adjacent to the settling passageways 86 and 88. The submerged gas volume is a sealed continuous gas volume, and internal walls of passageways 86 and 88 are vertically slotted to accommodate the baffle length. The uppermost liquid level is limited by the elevation of outlet port 92 and the lowest most vertical liquid level by the top of the internal upflow partially fluidized reactor 80. The baffled volume has two purposes. First, the gasified particles rising through the upflow partially fluidized bed 80, are stripped of their attached gases as they fall through the submerged gas volume, enabling the degasified particles to easily settle in the outer passageways 86 and 88. Secondly, the gas volume provides for variable reactor liquid volume while maintaining a consistent overhead gas phase pressure.

As the liquid level in the first reactor 18 falls due to the loss of volume in the second reactor 16, the pressure regulator transfers gas from the submerged baffled volume 82 and 84 to the overhead gas space equivalent to the amount of liquid volume lost. The pressure swing operation causes the loss in system volume. Therefore, the two-stage system is in a perpetual state of either increasing or decreasing in digestion volume. For design purposes, the reactor volume lost during the compression phase in the second reactor 16 is used to size the baffled volume in the first reactor 18. The cyclic operation produces an effluent substantially free of suspended solids exiting at line 92 and a thickened solid concentrate exiting at 78 of the first reactor 18. Referring to FIG. 5, the tank cover is closed by a fixed cover 102 at the upper end thereof where the gas outlet 94 is located. The clarified supernatant liquid outlet 92 is located in passageway 86 or 88 and the gas is released through outlet 94. An internal fixed volume with the device shown in FIGS. 5c–d is more reliable for volume correction since it has fewer moving parts. However, an internal floating roof, as shown in FIGS. 5e–f, can be substituted for the fixed baffle assembly depicted in FIGS. 5c–d for larger variable volume applications. In the floating roof design shown in FIGS. 5e–f, the floating pontoon assembly 98 can be weighted to add pressure to the gas submerged volume, which gives the first reactor 18 expandable storage capability needed to accommodate and equalize widely fluctuating volume and pressure applications.

The interstitial liquid within the partially fluidized bed 80 flows upward in the first reactor tank 18 in the direction shown by the arrows on the dashed lines shown in FIG. 1. Tank 18 is maintained at approximately atmospheric pressure. The flow velocity $V_f$ must be significantly less than the settling velocity of the suspended fraction $v_s$; otherwise the solids liquid separation significantly deteriorates, and solids capture by the system is less than optimum. Gas produced by anaerobiosis collects under baffled region 82 and 84, forming and holding a submerged gas volume. As the slurry mixture tops the weir elevation and falls over the weir, the contact with the submerged gas volume assists in stripping the biogas from the digesting particles. The clarified effluent flows out through the outlet 94. Gas stripping enables the solid particles to be concentrated both by bioflocculation and by gravity sedimentation in the outer passageways, and then be withdrawn before they can regasify and rise through the clarified water column. Concentrated and partially digested sludge from the tank 18 is recycled by the pump 34 to the inlet 26 of the second reactor tank 16. The recycle rate through the pump 32 is sufficient to turn over the complete system volume approximately once per day.

The concentrated solids from the first reactor 18 comprise biomass, organic particulate and colloidal solids that have not been hydrolyzed, a high concentration of anaerobic bacteria, and inorganic precipitates such as metal sulfides, struvite, phosphates, and other complex precipitates. The organic particulate and colloidal constituents in line 26 are the more slowly hydrolyzed and degraded materials that composed the influent stream 14. The organic particulate and colloidal constituents with anaerobic bacteria are confined in a gas suspension created in the second anaerobic reactor 16 via an applied vacuum for a period sufficient to nearly completely hydrolyze and metabolize the constituents. The second anaerobic reactor is constructed to withstand at least a one-atmosphere pressure swing between 0.5 atmosphere and 1.5 atmospheres. The enriched anaerobic microbial culture found there will cause a rapid hydrolysis of more slowly metabolizable constituents. The improvement of plasticization allows the volume of this second reactor 16 to be reduced in size to about one-third the size of the first anaerobic reactor 18. The quantity of biomass temporarily stored and digesting in the second anaerobic reactor 16 affects the system hydraulic retention time, which is determined by the rate of decomposition of plasticized particulates as well as the mass of anaerobic bacteria required to hydrolyze of influent substrate from the first anaerobic reactor 18. The hydraulic retention time in the second anaerobic reactor 16 may also be affected by the accumulation of anaerobic decomposition products such as ammonia and sulfide and mineralized solids.

Process efficiency can be improved by drawing the vacuum on the second reactor 16 at the position of vacuum pump 32 on line 22, as shown in FIGS. 2a–b. At this position, it is easier to control both the vacuum and pressure cycling swings across the second reactor 16 and the flow velocity to the first reactor along line 74, which feeds the upflow velocity in the partially fluidized bed 80. The relocation of pump 32 from line 72 to line 22 prevents wasting energy in separating out influent dissolved gases, thus preventing additional nitrogen and ammonia gases from contaminating the biogas at outlet 70. Decreasing the amount of nitrogen and ammonia improves the methane quality of the biogas stream 70 and reduces the formation of nitrous oxide air pollutants during biogas combustion. Nitrogen and ammonia gases produce undesirable photochemical smog on combustion.

The removal of mineralized solids from digestion is important to prevent the accumulation over time of spent solid, which would occupy a portion of digestion space needed for active digestion. If these solids are not removed, the mineralized solids will eventually accumulate to a point where the digestion mechanism and the performance of the system is impaired. The quantity of waste solids is a function of the influent inorganic solids content together with the portion that dissolves during fermentation and plasticization and exits the system via system effluent line 92. Since the inorganic solids accumulate slowly, they will normally need to be removed from the apparatus only intermittently.

As already discussed, the process of the invention entails a simple particle classification by weight, using buoyancy provided by rising gas bubbles discharged during the blowdown phase of the pressure cycle, as shown in FIG. 3. This method effectively separates heavy residual particles from the lighter volatile particles through the release of temporarily stored biogas accumulated during the pressure plasticization phase. In this way, certain soluble constituents that contain hydrophobic structures such as organic acids, proteins, enzymes and lighter particulate matter can be separated from the heavier inorganic particles by buoyancy provided by the rising gas surge. Increased removal of such constituents can be accomplished by increasing the gas bubble surface area through utilization of fine gas bubbles or increasing gas/solids ratios. It is understood that separation aids or chemicals may be used to help accomplish or improve the separation. If, on the other hand, non-chemically aided micro-bubble floatation is used, the method must be capable of producing a recycle concentrate substantially composed of undigested volatile solids and an underflow principally composed of mineralized or inorganic solids.

FIGS. 6a–d illustrate the preferred process for removal of the concentrated inorganic solids, wherein valves 58 and 56, sludge pump 54, pump bypass line 72, recycle line 62, and discharge line 76 comprise the assembly positioned at the bottom of the second reactor 16. The concentration of spent solids provides an opportunity for effective particle separation by simple density classification using only the rising blowdown gases. This procedure is preferred for its simplicity, but it is recognized that the separation of undissolved inorganic materials can be accomplished by any number of different differential density classification technologies such as centrifuges, hydrocyclones, and cyclones.

Figure 6A:
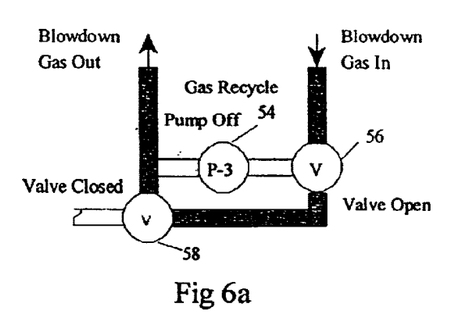
FIGS. 6a–d schematically illustrate four modes of a process for removal of the concentrated inorganic solids from the digester apparatus of the present invention.
Figure 6B:
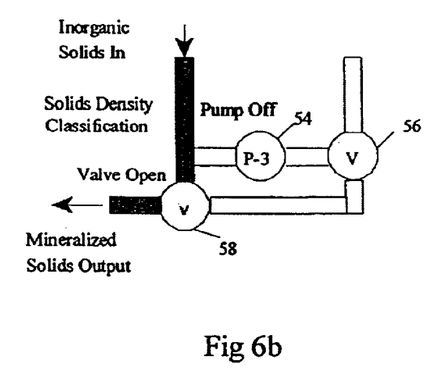
Figure 6C:
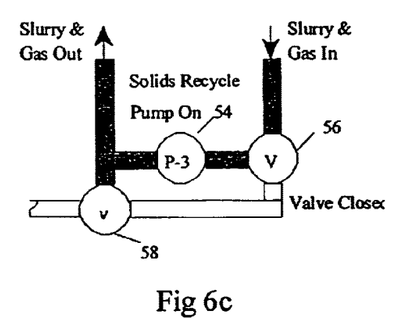
Figure 6D:
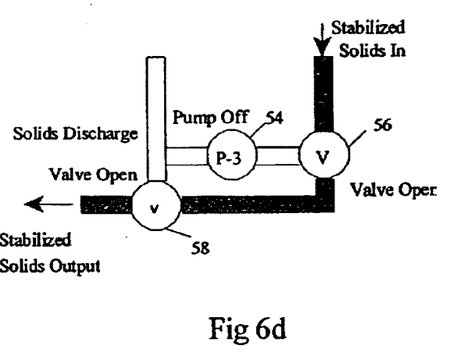

In the four modes of removing the inorganic solids in accordance with the present invention, illustrated in FIGS. 6a–d, the operation of the valves and pump are controlled by computer 300 to open or close, turn on or off, at a precise time and for a precise time duration, depending on the operation mode. The first two operational modes, shown in FIGS. 6a–b, are sequentially used to prevent inorganic solid accumulation in the system. A gas blowdown event, i.e., release of the gas pressure in reactor tank 16, produces a rapid gas discharge of accumulated digestive gases under pressure. During this event, the heavier inorganic particles fall rapidly through rising bubbles, whereas lighter organic floc will rise via bubble buoyancy. The components of the slurry mixture in line 62 are classified according to their respective specific gravities by the rising gases released when valve 56 opens and valve 58 closes. Eventually, the rising gases exit the system via gas outlet 70. The result is particulate stratification, whereby the heavier mineralized solids are located at the bottom of line 62 and the lighter solids fraction is carried upward via gas buoyancy. Referring to FIG. 6b, the hydrostatic pressure in line 62 can be used to expel the heavier mineralized solids at the bottom by opening valve 58 and closing valve 56 following blowdown. The valve discharge is timed to remain open only long enough to discharge the mineralized solids layer. The intermittent discharge of inorganic and mineralized solids via this method is typically conducted once per week for normal sewage sludge feedstocks. The light suspended, colloidal and particulate constituents, bacteria and inorganic precipitates separated from the soluble constituents are recycled, being delivered to the first anaerobic reactor 18 via line 62 when the third mode of operation begins. Referring to FIG. 6c, the third mode of operation is the recycling of the bottom solids back to the rest of the system to reseed these solids that have undergone repeated cyclic decompression and rapid hydrolysis, as shown in FIG. 3. Also, these solids effectively weight the gravity separation of solids in the outer separation chambers 86 and 88 that follow the upflow partially fluidized bed 80. It is preferable to have the solids content of the material influent line 74 as high as possible because the more concentrated the solid feed stream is, the smaller the first anaerobic reactor 18 need be, provided the higher concentration of solids does not inhibit the anaerobic bioactivity from accumulating dissolved byproducts of digestion. Referring to FIG. 6d, the fourth mode of operation is the hydrostatic removal of stabilized solids from the system in the case where production of stabilized soil conditioning solids for land application is desired or if solids need to be prematurely wasted from the system to reduce the effects of inhibitory conditions.

In accordance with the present invention, both reactors of the pressure swing digestion system preferably maintain a consistent fermentation temperature in either the mesophilic or thermophilic range. The temperature is controlled in the range of, preferably, about 20° C. to about 60° C., a temperature of about 35° C. being especially preferred. Both of the reactors shown in FIGS. 2a–b have double inner and outer wall insulation to prevent heat loss to the environment. Either heated water or exhaust gas from an engine-generator set can be used as the heat transfer fluid that flows through the jacketed volume to make up the environmental heat loss. Although other heat exchange methods such as external sludge or mixed liquor heat exchange or gas heat exchange can be used, they are less favorable because they require the removal of liquid and/or gases which disturb the preferred dispersive plug flow hydraulic regime.

Preferably, the gas outlet line 62 extends to intersect manifold line 14 on the discharge side of pump 20 to scrub the ammonia and sulfur-containing gases from the biogas stream. If ammonia and hydrogen sulfide are produced in small enough quantity, their dissolved and recycled species will not inhibit digestion in first reactor tank 18. It is particularly desirable to scrub these gas constituents out of the biogas stream on the pressure side of the process, thereby removing them from the combustion fuel mixture. Further reduction in sulfur from the product gas streams 70 and 94 can be accomplished by providing either a soluble or liquid sulfur scavenger system at 112. This is particularly useful for CHP applications.

The preferred embodiment of the two-stage digestion process of the present invention reduces the ammonia and sulfide toxicity problems recognized to exist with conventional methane digesters, either single or multiple stage system designs. The two digestion reactors operate in a closed loop, with pressure swing digester tank 16 passing its recycle effluent to the concentrator digester tank 18, liquid being separated from the gravity thickened solids, which are then returned to the digester tank 16 while liquid effluent 92 is continuously discharged. This process substantially reduces the concentration of ammonia and sulfide and prevents toxicity problems. If necessary, additional water can be added to recycle line 26 or 74 to dilute the products of digestion and prevent interference with anaerobic bioactivity.

The apparatus and process of the present invention improve both the speed of digestion and completeness of conversion, which greatly improves the process economic feasibility. The capital and operating costs are reduced by a decrease in hydraulic retention time, a decrease in system reactor volume, and complete conversion of the feed. Referring to FIGS. 2a–b, note that the cost of removing the solids in the first reactor 18 is based on the minimum hydraulic detention time of the reactor while maintaining a high solids capture ratio. The quantity of solids recycled from the first reactor 18 dictates the size and capital cost of the second reactor 16. The preferred economic decision point will be where the easily hydrolyzed solids are successfully removed in the first reactor 18, while the soluble or nonparticulate constituents discharged through line 92 and the more slowly hydrolyzed solids are completely removed in the second reactor 16. The combination of great improvements in speed and conversion completeness enables a much smaller system tankage and therefore much improved capital economics and process feasibility.

From the foregoing description, it is apparent that the present invention provides an improved apparatus and process for the anaerobic digestion of organic biomass materials such as sewage sludge or biomass. While exemplary forms of the system and the best mode for its operation have been described, it will be appreciated that variations and modifications can be effected within the spirit and scope of the invention, which is defined by the claims that follow.

What is claimed is:

1. An improved digester apparatus for converting wet carbonaceous biomass materials to biogas comprising gaseous organic fuel, said apparatus comprising a digestion unit operating at a controlled temperature and having a concentrator component and a pressure swing component each containing anaerobic bacteria; means for conveying slurried aqueous biomass from a biomass source to said concentrator component; means for removing said biogas from said concentrator component; means for conveying concentrated aqueous biomass from said concentrator component to said pressure swing component and means for conveying digested aqueous biomass from said pressure swing component to said concentrator component, thereby forming a closed loop between said concentrator and pressure swing components; means for removing waste solids from said pressure swing component; and pressure swing pump means for controlling the pressure within said pressure swing component in a cycle comprising a first phase having a first time duration at a sub-atmospheric first pressure and a second phase having a second time duration and a second pressure at or above atmospheric pressure; wherein the improvement comprises:

inclusion in said apparatus of programmable computer means provided with a database comprising previously acquired data relating biomass-biogas conversion for biomass materials of varying compositions to values for said first and second, respectively, pressures and time durations of said first and second phases, said programmable computer means for continuously monitoring the pressure of biogas in said pressure swing component and to adjust said first and second phases in said cycle of said pressure swing pump means to optimize biogas conversion of biomass from said biomass source.

2. The apparatus of claim 1 wherein said means for conveying is selected from the group consisting of pipelines, valves, pumps, and combinations thereof.

3. The apparatus of claim 1 wherein said means for conveying concentrated aqueous biomass from said concentrator component to said pressure swing component and said means for conveying digested aqueous biomass from said pressure swing component to said concentrator component each comprises a pump.

4. The apparatus of claim 3 wherein said computer means operates to control each said pump.

5. The apparatus of claim 1 wherein said means for removing waste solids from said pressure swing component comprises a valve and a pump.

6. The apparatus of claim 5 wherein said computer means operates to control said valve and said pump.

7. The apparatus of claim 1 wherein said concentrator and pressure swing components are included in a single tank.

8. The apparatus of claim 1 wherein each of said concentrator and pressure swing components comprises a separate tank.

9. The apparatus of claim 8 wherein each said tank comprises a baffle assembly disposed in an upper portion of said tank.

10. The apparatus of claim 8 wherein said tank comprising said pressure swing component is provided with a blowdown valve for relieving gas pressure, said blowdown valve being disposed at a bottom portion of said tank.

11. The apparatus of claim 1 wherein said pressure swing pump means comprises a vacuum pump provided with a drive motor.

12. The apparatus of claim 1 wherein said computer means comprises a proportional, integral, and differential (PID) programmable controller.

13. The apparatus of claim 1 wherein said computer means further comprises a linear pressure transducer.

14. The apparatus of claim 1 wherein said pressure in said pressure swing component varies between about 0.5 atmosphere and about 1.5 atmospheres.

15. The apparatus of claim 1 wherein said first and second time durations are each about one hour to about 4 hours.

16. The apparatus of claim 1 wherein said controlled temperature is about 35° C.

17. The apparatus of claim 1 wherein said biomass source comprises cellulose.

18. The apparatus of claim 1 wherein said biogas is a gas selected from the group consisting of methane, carbon dioxide, nitrogen, ammonia, hydrogen sulfide, and mixtures thereof.

19. The apparatus of claim 1 wherein said gaseous organic fuel comprises methane.

20. A system for converting wet carbonaceous biomass materials to biogas comprising gaseous organic fuel, said system comprising a gas storage and cleanup unit, a combustion engine-generator set, an exhaust gas heat exchanger, and the digester apparatus of claim 1.

21. A process for converting wet carbonaceous biomass materials to biogas comprising gaseous organic fuel, said process comprising:

providing a digester apparatus comprising a digestion unit operating at a controlled temperature and having a concentrator component and a pressure swing component each containing anaerobic bacteria;

conveying slurried aqueous biomass from a biomass source to said concentrator component, concentrating said biomass therein, and removing biogas therefrom;

conveying concentrated aqueous biomass from said concentrator component to said pressure swing component, and conveying digested aqueous biomass from said pressure swing component to said concentrator component, thereby forming a closed loop between said concentrator and pressure swing components; and controlling pressure within said pressure swing component in a cycle effected by pressure swing pump means and comprising a first phase having a first time duration at a sub-atmospheric first pressure and a second phase having a second time duration and a second pressure at or above atmospheric pressure, said pressure swing pump means being controlled by programmable computer means provided with a database comprising previously acquired data relating biomass-biogas conversion for biomass materials of varying compositions to values for said first and second, respectively, pressures and time durations of said first and second phases, wherein said programmable computer means continuously monitors the pressure of biogas in said pressure swing component and adjusts said first and second phases in said cycle to optimize biogas conversion of biomass from said biomass source.

22. The process of claim 21 further comprising: removing waste solids from said pressure swing component.

23. The process of claim 21 wherein said slurried aqueous biomass from said biomass source contains bacterial pathogens, and said waste solids are substantially free of bacterial pathogens.

24. The process of claim 21 wherein said computer means further operates to control a pump for conveying concentrated aqueous biomass from said concentrator component to said pressure swing component and a pump for conveying digested aqueous biomass from said pressure swing component to said concentrator component.

25. The process of claim 21 wherein said computer means further operates to control a valve and a pump for removing said waste solids from said pressure swing component.

26. The process of claim 21 wherein said concentrator and pressure swing components are included in a single tank.

27. The process of claim 21 wherein each of said concentrator and pressure swing components comprises a separate tank.

28. The process of claim 27 wherein each said tank comprises a baffle assembly disposed in an upper portion of said tank.

29. The process of claim 28 wherein said baffle assembly confines a submerged gas volume substantially equal to a volume of biogas removed from said concentrator component.

30. The process of claim 27 wherein said tank comprising said pressure swing component is provided with a blowdown valve for relieving gas pressure, said blowdown valve being disposed at a bottom portion of said tank.

31. The process of claim 21 wherein said pressure swing pump means comprises a vacuum pump provided with a drive motor.

32. The process of claim 21 wherein said computer means comprises a proportional, integral, and differential (PID) controller.

33. The process of claim 21 wherein said computer means further comprises a linear pressure transducer.

34. The process of claim 21 wherein said pressure in said pressure swing component varies between about 0.5 atmosphere and about 1.5 atmospheres.

35. The process of claim 21 wherein said first and second time durations are each about one hour to about 4 hours.

36. The process of claim 21 wherein said controlled temperature is about 20° C. to about 60° C.

37. The process of claim 36 wherein said controlled temperature is about 35° C.

38. The process of claim 21 wherein said biomass source comprises cellulose.

39. The process of claim 21 wherein said biogas is a gas selected from the group consisting of methane, hydrogen, carbon dioxide, nitrogen, ammonia, hydrogen sulfide, and mixtures thereof.

40. The process of claim 21 wherein said gaseous organic fuel comprises methane.

* * * * *